United States Patent
Bonrath et al.

(10) Patent No.: US 9,227,907 B2
(45) Date of Patent: Jan. 5, 2016

(54) ACID CHLORIDE

(75) Inventors: Werner Bonrath, Basel (CH); Thomas Netscher, Basel (CH); Jan Schütz, Basel (CH); Bettina Wüstenberg, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 97 days.

(21) Appl. No.: 14/128,751

(22) PCT Filed: Jun. 14, 2012

(86) PCT No.: PCT/EP2012/061265
§ 371 (c)(1),
(2), (4) Date: Aug. 6, 2014

(87) PCT Pub. No.: WO2012/175395
PCT Pub. Date: Dec. 27, 2012

(65) Prior Publication Data
US 2014/0350289 A1    Nov. 27, 2014

(30) Foreign Application Priority Data
Jun. 22, 2011 (EP) .................................... 11171067

(51) Int. Cl.
| | |
|---|---|
| *C07C 67/02* | (2006.01) |
| *C07C 69/65* | (2006.01) |
| *C07C 67/287* | (2006.01) |
| *C07C 69/63* | (2006.01) |
| *C07C 67/00* | (2006.01) |

(52) U.S. Cl.
CPC .................. *C07C 69/65* (2013.01); *C07C 67/00* (2013.01); *C07C 67/287* (2013.01); *C07C 69/63* (2013.01)

(58) Field of Classification Search
CPC ...... C07C 67/287; C07C 69/63; C07C 67/00; C07C 69/65
See application file for complete search history.

(56) References Cited

U.S. PATENT DOCUMENTS

| | | | |
|---|---|---|---|
| 3,876,673 A * | 4/1975 | Julia | 554/127 |
| 4,064,162 A | 12/1977 | Oroshnik | |
| 9,067,877 B2 * | 6/2015 | Bonrath et al. | |

OTHER PUBLICATIONS

International Search Report for PCT/EP2012/061265, mailed Sep. 27, 2012.
Ried et al., "Neue, potentiell bakteriostatisch und fungistatisch wirksame Stoffe auf der Basis des 5-Methoxypent-4-en-2-in-1-ons bzw.-1-imins", *Archiv Der Pharmazie*, vol. 316, No. 5, Jan. 1, 1983, pp. 454-460.
Duvall et al., "Structure Reassignment and Synthesis of Jenamidines A1/A2, Synthesis of (+)-NP25302, and Formal Synthesis of SB-311009 Analogues", *Journal of Organic Chemistry*, vol. 71 (22) Oct. 2006, pp. 8578-8590.

* cited by examiner

*Primary Examiner* — Yevegeny Valenrod
*Assistant Examiner* — Blaine G Doletski
(74) *Attorney, Agent, or Firm* — Nixon & Vanderhye P.C.

(57) ABSTRACT

The present invention relates to new organic compounds, to their synthesis as well as to their use in organic synthesis, especially in processes forming intermediates (building blocks) for the synthesis of vitamin A or β-carotene or other carotenoids.

9 Claims, No Drawings

ACID CHLORIDE

This application is the U.S. national phase of International Application No. PCT/EP2012/061265 filed 14 Jun. 2012 which designated the U.S. and claims priority to EP Patent Application No. 11171068.7 filed 22 Jun. 2011, the entire contents of each of which are hereby incorporated by reference.

The present invention relates to new organic compounds, to their synthesis as well as to their use in organic synthesis, especially in processes forming intermediates (building blocks) for the synthesis of vitamin A or β-carotene or other carotenoids, e.g. lycopene, canthaxanthin, zeaxanthin or astaxanthin.

The new compounds are acid chlorides, which can be applied as building blocks in organic synthesis. Especially to be mentioned is that the new acid chlorides are useful as starting materials for the synthesis of vitamin A or β-carotene. The acid chlorides are used to forming intermediates (building blocks), which are used to produce vitamin A (and its derivatives) or β-carotene.

Vitamin A

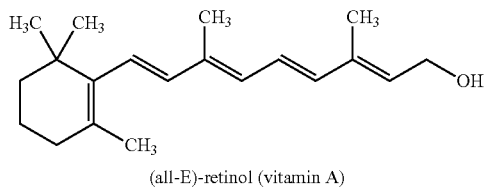 [SMILES: CC1=C(/C=C/C(C)=C/C=C/C(C)=C/CO)C(C)(C)CCC1]

(all-E)-retinol (vitamin A)

is an important ingredient for many applications. Vitamin A plays a role in a variety of functions throughout the body, such as e.g. vision process, gene transcription, immune function, bone metabolism, haematopoiesis, skin and cellular health and antioxidant function.

Due to the importance of vitamin A (and its derivatives) and the complexity of the synthesis thereof, there is always a need for improved processes of production.

The goal of this invention was to find new and easy to produce compounds which are used in an improved synthesis of vitamin A and its derivatives. It was found that the new organic compounds allow simplifying the process of production of vitamin A and its derivatives.

Therefore the present invention relates to compounds of formula (I)

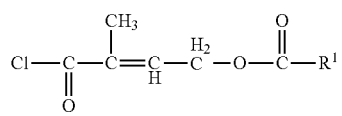

wherein $R^1$ signifies a $C_1$-$C_{15}$ alkyl moiety or a $C_2$-$C_{18}$ alkenyl moiety.

When $R^1$ is a $C_1$-$C_{15}$ alkyl moiety, then preferably the alkyl moiety is linear. Especially preferred alkyl moieties are methyl, ethyl and pentadecyl.

When $R^1$ is a $C_2$-$C_{18}$ alkenyl moiety, there are one or more C—C double bonds. Preferably the alkenyl moiety is unbranched.

Compounds of formula (I) can be in the Z- or E-form as well as a mixture of both.

These most preferred compounds of formula (I) are listed below (compounds of formula (Ia), (Ib) and (Ic)):

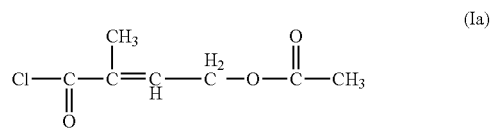

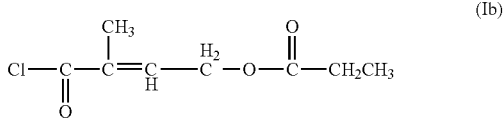

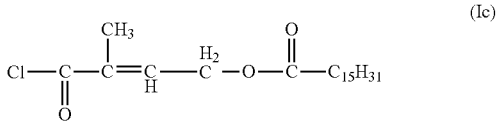

As mentioned above the advantage of these compounds is that they are easily obtainable and they can be used in the synthesis of intermediates for the vitamin A or β-carotene synthesis, especially for the synthesis of vitamin A (and its derivatives).

The compounds of formula (I) can be produced by chlorination of compounds of formula (II)

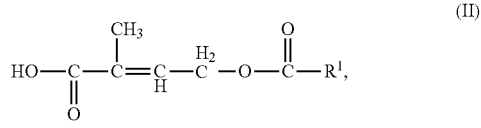

wherein $R^1$ has the same meaning as for formula (I).

Therefore a further embodiment of the present invention relates to a process of production of compounds of formula (I)

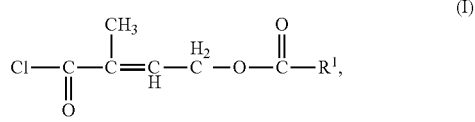

wherein $R^1$ signifies a $C_1$-$C_{15}$ alkyl moiety or a $C_2$-$C_{18}$ alkenyl moiety, wherein compounds of formula (II)

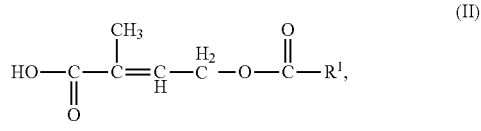

wherein $R^1$ signifies a $C_1$-$C_{15}$ alkyl moiety or a $C_2$-$C_{18}$ alkenyl moiety are chlorinated using at least one chlorinating agent.

All preferences given for $R^1$ above for the compounds of formula (I) also apply for compounds of formula (II).

Chlorinating agents are widely known and used. For the process according to the present invention any chlorinating agent (or mixtures thereof) can be used.

Examples of chlorinating agents are oxalylchloride, phosphorus pentachloride, thionylchloride, phosphorus oxychloride, chlorine, chloric acid, antimony(V) chloride, hypochlorous acid, N-chlorosuccinimide, phosphorus trichloride, sulfurylchloride, carbon tetrachloride, or cyanuric chloride.

Preferred chlorinating agents are oxalylchloride, phosphorus pentachloride, thionylchloride and phosphorus oxychloride.

Therefore a preferred embodiment of the present invention relates to a process of production of compounds of formula (I)

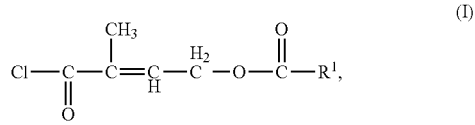
(I)

wherein $R^1$ signifies a $C_1$-$C_{15}$ alkyl moiety or a $C_2$-$C_{18}$ alkenyl moiety, wherein compounds of formula (II)

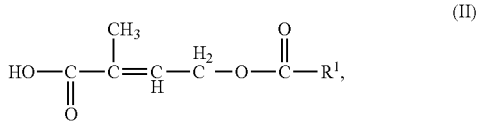
(II)

wherein $R^1$ has the same meanings as in formula (I), are chlorinated using at least one chlorinating agent chosen from the group consisting of oxalylchloride, phosphorus pentachloride, thionylchloride and phosphorus oxychloride.

The chlorinating agents are usually added in a slight molar excess in regard to the amount of compound of formula (II).

The reaction is usually carried out in polar or non-polar solvents like toluene, N,N-dimethylformamide (DMF), dichloromethane, dichloroethane, 1-methyl-2-pyrrolidone (NMP), xylenes, or ethers.

The process of production of the compounds of formula (I) according to the present invention is usually carried out at temperature of from −20° C. to 100° C., preferably from 0° C. to 50° C.

The process of production of the compounds of formula (I) according to the present invention has a reaction time which is usually between 1 and 5 hours.

At the end of the reaction the solvent is removed by distillation (usually under reduced pressure).

The obtained products (compounds of formula (I)) are purified using conventional methods. But it is also possible that the obtained product is used in further reactions without purification.

The compounds of formula (I) can be used in organic synthesis. Preferably the compounds of formula (I) as described above are used to form intermediate compounds for the synthesis of vitamin A (and its derivatives) and β-carotene (preferably vitamin A).

In a following reaction a compound of formula (III)

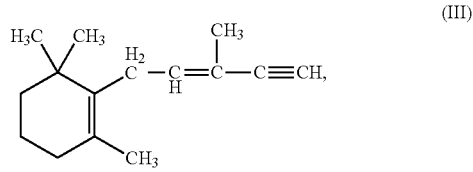
(III)

which can be produced according to a method disclosed in GB 1034189, which is therefore incorporated by reference, is reacted with a compound of formula (I)

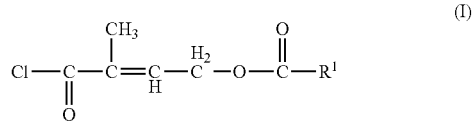
(I)

as disclosed and described above.

The reaction product of this reaction is a compound of formula (IV)

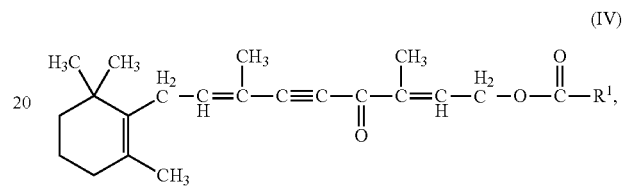
(IV)

wherein $R^1$ has the same meanings (and preferences) as defined above.

The compounds of formula (IV) are used as intermediates in the synthesis of vitamin A (and its derivatives) and β-carotene, preferably in the synthesis of vitamin A (and its derivatives).

The following examples serve to illustrate the invention.

EXAMPLES

Example 1

4-chloro-3-methyl-4-oxobut-2-enyl acetate (Compound of formula (Ia))

3.2 g (19.73 mmol) of 2-methyl-4-acetyloxy-2-butenoic acid (compound of formula (IIa)

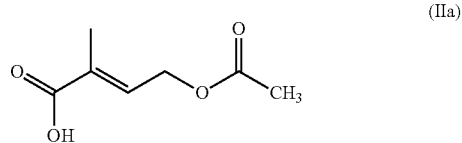
(IIa)

was mixed with 11.4 ml of toluene and 300 µl of N,N-dimethylformamide (DMF). 2.78 g (21.70 mmol) of oxalylchloride was slowly added to the reaction mixture while keeping the temperature of the reaction mixture with a water bath at 20° C. After 2.5 hours of stirring at room temperature, the solvent was removed at 50° C. and 30 mbar. A red-brownish oil (3.83 g) was obtained which was purified. A slightly yellow liquid was obtained. The yield of 4-chloro-3-methyl-4-oxobut-2-enyl acetate (compound of formula (Ia)) was 99%.

Example 2

4-chloro-3-methyl-4-oxobut-2-enyl acetate (Compound of formula (Ia))

0.5 g (2.86 mmol) of 2-methyl-4-acetyloxy-2-butenoic acid (compound of formula (IIa)) was mixed with dichloromethane (5.0 ml). 0.73 g (3.43 mmol) of phosphorus pentachloride was slowly added to the reaction mixture while keeping the temperature of the reaction mixture with a water bath at 15° C. The reaction mixture was allowed to warm to room temperature and stirred for 1.75 hours. Then the solvent was removed at 50° C. and 30 mbar and a colourless liquid was obtained. The yield of 4-chloro-3-methyl-4-oxobut-2-enyl acetate (compound of formula (Ia)) was 97%.

Example 3

3,7-dimethyl-4-oxo-9-(2,6,6-trimethylcyclohex-1-enyl)nona-2,7-dien-5-ynyl acetate (compound of formula (IVa))

Under nitrogen atmosphere 59.9 mg (0.308 mmol) of copper(I) iodide and 110.3 mg (0.154 mmol) of bis(triphenylphosphine)palladium(II) dichloride [(PPh$_3$)$_2$PdCl$_2$] were added to a 100 ml four-necked flask. At 23° C., 42.0 ml of anhydrous THF was added and the yellow suspension was stirred for 5 min. When 2.15 ml (15.4 mmol) of triethylamine were introduced drop wise via syringe an orange solution was obtained. Within 1 minute 3.10 g (15.4 mmol) of 4-chloro-3-methyl-4-oxobut-2-enyl acetate (compound of formula (Ia)) were added and the solution turned dark orange. Upon drop wise addition of 2.92 g (14.0 mmol) of 1,3,3-trimethyl-2-(3-methylpent-2-en-4-ynyl)cyclohex-1-ene (compound of formula (III))

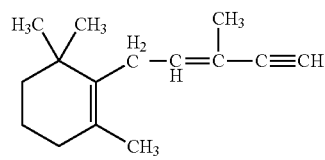

over 5 minutes a yellow suspension was formed. The reaction mixture was cooled to room temperature and monitored by GC and TLC. After 2 hours and 20 min at 23° C., all starting material was consumed. The reaction mixture was transferred into a separatory funnel, diluted with 80 ml of diethyl ether and washed with semi-concentrated sodium bicarbonate solution (80 ml). The layers were separated and the aqueous layer was extracted with diethyl ether (2×75 ml). The combined organic layers were washed with 80 ml of semi-sat. sodium bicarbonate solution, dried over sodium sulphate and concentrated to dryness. The crude product (compound of formula (IVa))

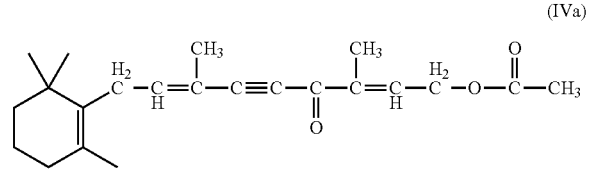

was obtained as brown oil (5.44 g, 82% purity, 93% yield) and purified by column chromatography and charcoal treatment.

The invention claimed is:

1. A compound of formula (I)

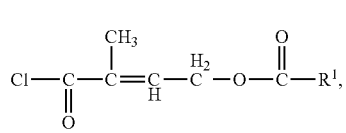

wherein $R^1$ signifies a $C_1$-$C_{15}$ alkyl moiety or a $C_2$-$C_{18}$ alkenyl moiety.

2. Compound according to claim 1, wherein $R^1$ is a linear $C_1$-$C_{15}$ alkyl moiety.

3. Compound according to claim 1, wherein $R^1$ is methyl, ethyl and pentadecyl.

4. Compound according to claim 1, wherein the compound is in the Z-form or in the E-form.

5. Compound according to claim 1, wherein the compound is a mixture of the Z- and E-form.

6. Process of production of compounds of formula (I) according to claim 1, characterised in that a compound of formula (II)

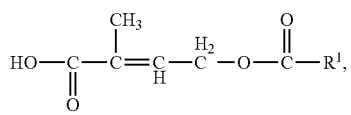

wherein $R^1$ has meanings as defined in claim 1, is chlorinated using at least one chlorinating agent.

7. Process according to claim 6 wherein the chlorinating agent is chosen from the group consisting of oxalylchloride, phosphorus pentachloride, thionylchloride, phosphorus oxychloride, chlorine, chloric acid, antimony(V) chloride, hypochlorous acid, N-chlorosuccinimide, phosphorus trichloride, sulfurylchloride, carbon tetrachloride and cyanuric chloride.

8. Process according to claim 6, wherein the chlorination reactant is chosen from the group consisting of oxalylchloride, phosphorus pentachloride, thionylchloride and phosphorus oxychloride.

9. Process according to claim 6, wherein the process is carried out in toluene, N,N-dimethylformamide (DMF), dichloromethane, dichloroethane, 1-methyl-2-pyrrolidone (NMP), xylenes, or ethers.

\* \* \* \* \*